United States Patent
Lee

(10) Patent No.: US 8,779,384 B2
(45) Date of Patent: Jul. 15, 2014

(54) CLEAN WATER DISPENSING DEVICE

(75) Inventor: Yeon Seok Lee, Hanam-si (KR)

(73) Assignee: Banpo Distribution Co., Ltd, Hanam-si, Gyeonggi-do (KR)

( * ) Notice: Subject to any disclaimer, the term of this patent is extended or adjusted under 35 U.S.C. 154(b) by 0 days.

(21) Appl. No.: 14/116,028

(22) PCT Filed: Apr. 23, 2012

(86) PCT No.: PCT/KR2012/003121
§ 371 (c)(1),
(2), (4) Date: Nov. 6, 2013

(87) PCT Pub. No.: WO2012/153923
PCT Pub. Date: Nov. 15, 2012

(65) Prior Publication Data
US 2014/0124680 A1    May 8, 2014

(30) Foreign Application Priority Data
May 12, 2011 (KR) .................. 10-2011-0044615

(51) Int. Cl.
*C02F 1/32* (2006.01)
*B67D 3/00* (2006.01)

(52) U.S. Cl.
USPC ........ 250/437; 250/436; 250/434; 250/432 R; 250/428; 250/429

(58) Field of Classification Search
USPC .............. 250/428, 429, 432 R, 434, 436, 437
See application file for complete search history.

(56) References Cited

U.S. PATENT DOCUMENTS

| | | | | |
|---|---|---|---|---|
| 4,757,921 | A * | 7/1988 | Snowball | 222/146.6 |
| 5,441,179 | A * | 8/1995 | Marsh | 222/190 |
| 5,871,620 | A * | 2/1999 | Haug et al. | 204/157.15 |
| 6,193,894 | B1 * | 2/2001 | Hollander | 210/748.11 |
| 6,419,821 | B1 * | 7/2002 | Gadgil et al. | 210/86 |
| 6,602,425 | B2 * | 8/2003 | Gadgil et al. | 210/744 |
| 6,786,255 | B1 * | 9/2004 | Lee | 141/351 |
| 7,641,790 | B2 * | 1/2010 | Maiden | 210/91 |
| 7,772,566 | B2 * | 8/2010 | Lee | 250/436 |
| 8,334,518 | B2 * | 12/2012 | Matsuda et al. | 250/436 |
| 8,614,425 | B2 * | 12/2013 | Conradt et al. | 250/455.11 |
| 2002/0083842 | A1 * | 7/2002 | Kown | 99/290 |
| 2004/0046127 | A1 * | 3/2004 | Wong | 250/437 |
| 2005/0228154 | A1 * | 10/2005 | Matsumoto et al. | 526/317.1 |

* cited by examiner

*Primary Examiner* — David A Vanore
(74) *Attorney, Agent, or Firm* — Nath, Goldberg & Meyer; Jerald L. Meyer

(57) ABSTRACT

A clean water dispensing device is disclosed. The device includes a pure water tank (10), a sterilization tube (20), a sterilization lamp (30) and a transit tube (32). The pure water tank is fitted into a cold water tank (5) in such a way that a closed space is defined between the cold water tank and the pure water tank. Drinking water is drawn into an inlet port of the sterilization tube and passes through the transit tube before being stored in the cold water tank through an outlet port of the sterilization tube. The closed space is prevented from making contact with outside air, and only drinking water that has been sterilized by the sterilization tube is supplied into the closed space. Therefore, even if cold water is stored in the closed space for a long period of time, there is little possibility of the propagation of bacteria.

3 Claims, 6 Drawing Sheets

CLEAN WATER DISPENSING DEVICE

This is a National Phase Application filed under 35 U.S.C. 371 as a national stage of PCT/KR2012/003121, filed Apr. 23, 2012, and claiming priority from Korean Application No. 10-2011-0044615, filed May 12, 2011, the content of each of which is hereby incorporated by reference in its entirety.

TECHNICAL FIELD

The present invention relates, in general, to clean water dispensing devices for cold and hot water dispensers or water purifiers and, more particularly, to a clean water dispensing device in which a pure water tank is fitted into a cold water tank in such a way that a closed space is defined between the cold water tank and the pure water tank, and which is configured such that only drinking water that has been sterilized by a sterilization tube is supplied into the closed space and cooled and stored therein so that a user can always drink clean sterilized water.

BACKGROUND ART

Generally, cold and hot water dispensers are water supply apparatuses which are installed in houses, offices, restaurants, etc. to conveniently provide cold or hot water to users. Such a cold and hot water dispenser heats water filtered by a filter or water supplied from a mineral water tank so as to provide hot water or cools it to provide cold water.

As shown in FIG. 1, a typical cold and hot water dispenser includes a casing 2, a cold water tank 5 which is disposed in an upper portion of the casing 2, and a hot water tank 7 which is disposed in a medial portion of the casing 2. The cold water tank 5 is a cylindrical tank which is closed on a lower end thereof and is open on an upper end thereof. A cooling coil 6 is wound around an outer circumferential surface of the cold water tank 5. A mineral water tank 1 is placed upside down on an upper surface of the casing 2 in such a way that an opening of the mineral water tank 1 is disposed in the open upper end of the cold water tank 5. The hot water tank 7 is a cylindrical tank which is closed on both upper and lower ends thereof. A heating coil 8 is wound around an outer circumferential surface of the hot water tank 7. A central portion of an upper end of the hot water tank 7 is connected to a central portion of a lower end of the cold water tank 5 by a connection pipe 3. Further, the cold water tank 5 and the hot water tank 7 are respectively connected at lower ends thereof to a cold water valve 51 and a hot water valve 52 by connection pipes 3.

Furthermore, a drain pipe 4 is connected to a lower end of the hot water tank 7. A distal end of the drain pipe is configured such that it is usually closed by a stopper, and when it is required to discharge water from the hot water tank 7, the distal end of the drain pipe 4 opens.

Water that is contained in the hot water tank 7 is heated by the heating coil 8 to a relatively high temperature. Therefore, it is difficult for bacteria to grow in the water in the hot water tank 7. However, because the upper end of the cold water tank 5 is open, cold water in the cold water tank 5 makes contact with the air in the casing 2, thus causing a problem of propagation of bacteria in the cold water. If cold water is stored in the cold water tank 5 for a long period of time, it provides a friendly environment for bacteria.

Furthermore, cold water discharged from the mineral water tank 1 is cooled in the cold water tank 5 by the cooling coil 6 before being supplied into the hot water tank 7 through the connection pipe 3. As such, because mineral water that has been cooled is supplied into and heated in the hot water tank 7, additional power consumption is required.

DISCLOSURE

Technical Problem

Accordingly, the present invention has been made keeping in mind the above problems occurring in the prior art, and an object of the present invention is to provide a clean water dispensing device in which a pure water tank is fitted into the cold water tank in such a way that a closed space is defined between the cold water tank and the pure water tank and is isolated from the outside air, and which is configured such that only drinking water that has been sterilized by a sterilization tube disposed in a pure water tank is supplied into the closed space, and is cooled and stored therein, so that even if cold water is stored in the closed space for a long period of time, there is little possibility for the propagation of bacteria.

Another object of the present invention is to provide a clean water dispensing device which can be easily coupled to a cold water tank of an existing cold and hot water dispenser or water purifier, whereby a problem of propagation of bacteria which occurs in the conventional cold and hot water dispenser or water purifier can be simply solved, and which is configured such that drinking water which has been contained in a pure water tank and not cooled, rather than cold water in the cold water tank, is supplied into the hot water tank so that consumption of power required to heat drinking water can be minimized.

Technical Solution

In order to accomplish the above objects, the present invention provides a clean water dispensing device for a cold and hot water dispenser or a water purifier, the clean water dispensing device including: a pure water tank containing drinking water therein, pure water tank being disposed in a cold water tank in such a way that a closed space is defined between the pure water tank and the cold water tank with cold water disposed in the closed space; a sterilization tube provided in the pure water tank, the sterilization tube having an inlet port that is open and an outlet port connected to the closed space through the pure water tank; a sterilization lamp disposed in the sterilization tube; and a transit tube spirally wound around an outer circumferential surface of the sterilization lamp, the transit tube being connected to the outlet port, wherein the drinking water that is contained in the pure water tank is drawn into the inlet port and passes through the transit tube before being supplied into the cold water tank through the outlet port and being stored in the cold water tank.

The sterilization tube may be placed upright in such a way that the inlet port is disposed at a lower position, and the outlet port is disposed at an upper position. The inlet port may be brought into close contact with a bottom of the pure water tank, and an inlet hole may be formed in the inlet port so that the drinking water is drawn into the sterilization tube through the inlet hole.

Advantageous Effects

In a clean water dispensing device according to the present invention, drinking water contained in a pure water tank must pass through a sterilization tube disposed in the pure water tank before being supplied into a closed space defined between a cold water tank and a pure water tank and stored in the closed space. Therefore, drinking water which is supplied into the closed space can be reliably sterilized. Because the closed space is airtightly sealed, it does not make contact with the outside air so that there is little possibility of propagation of bacteria.

Furthermore, the clean water dispensing device according to the present invention can be easily coupled to a cold water tank of an existing cold and hot water dispenser and water purifier. Thus, the present invention can simply solve the problem of propagation of bacteria which occurs in the conventional cold and hot water dispenser or water purifier. The replacement costs for the cold and hot water dispenser or water purifier can be markedly reduced. Moreover, drinking water which has been contained in the pure water tank and not cooled, rather than cold water which has been contained in the cold water tank, is supplied into the hot water tank. The consumption of power required to heat drinking water can be minimized. In an embodiment in which the sterilization tube is placed upright in the pure water tank, drinking water is drawn into a lower end of the sterilization tube and discharged out of the sterilization tube through an upper end thereof while overcoming the force of gravity. Therefore, the time period for which drinking water is in the sterilization tube is increased, thus further enhancing the sterilization effect.

BEST MODE

Figure 1:
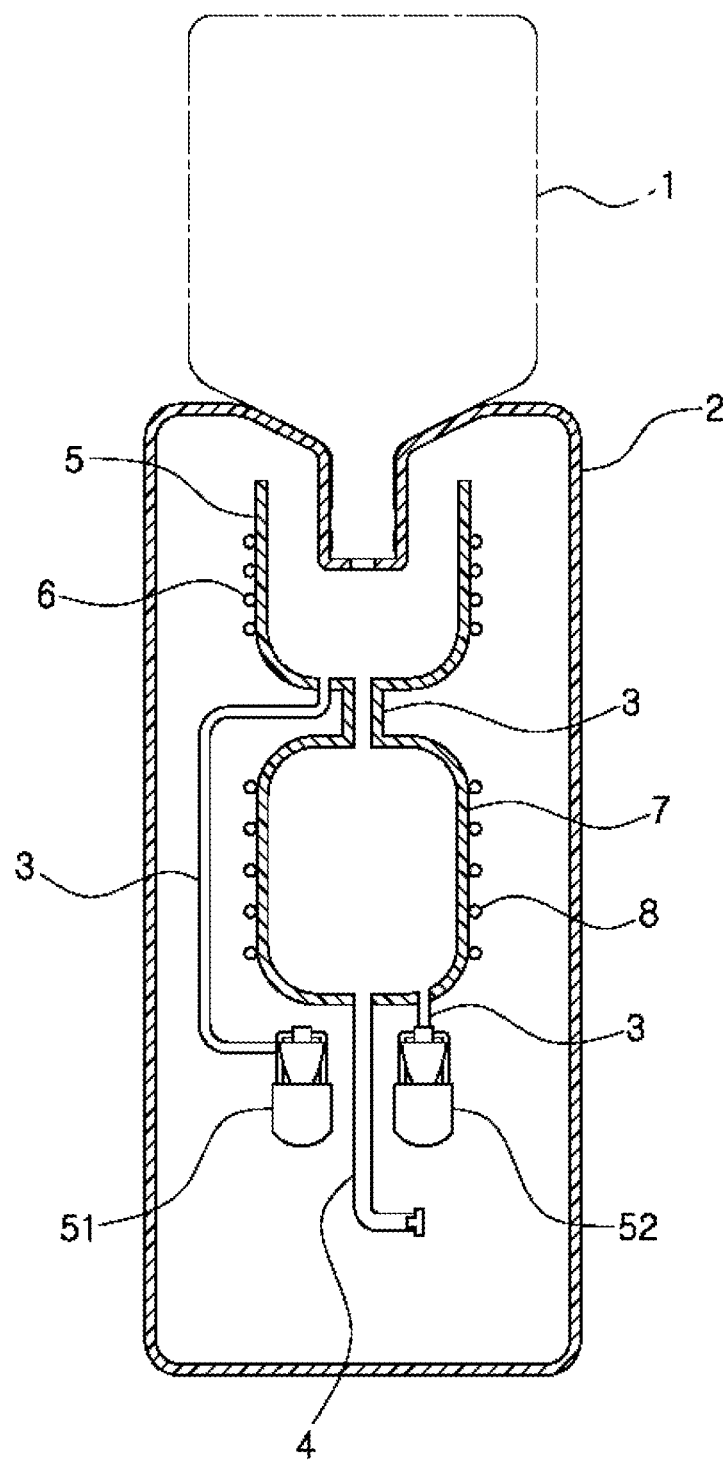
FIG. 1 is a schematic sectional view of a conventional cold and hot water dispenser.
Figure 2:
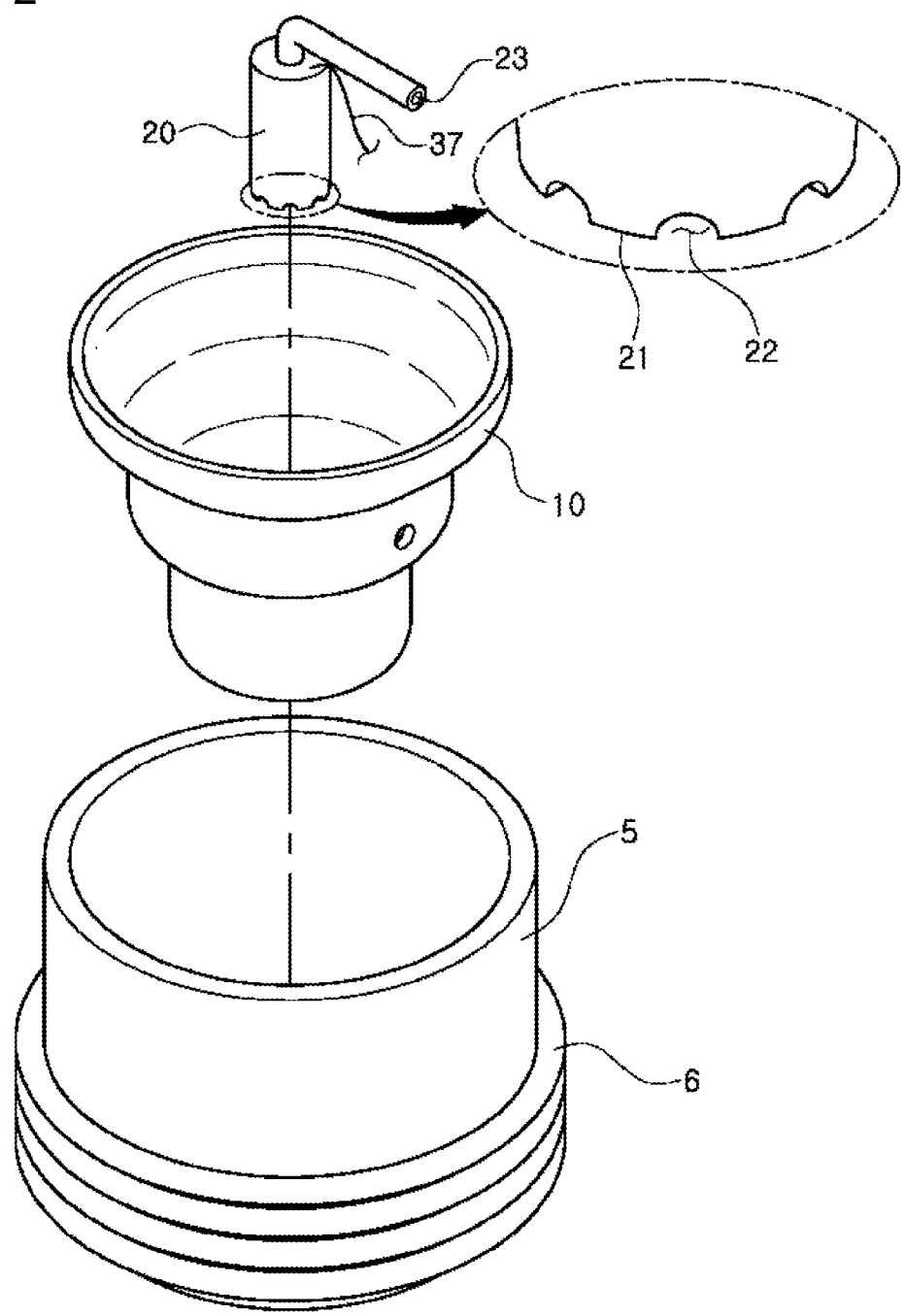
FIG. 2 is an exploded perspective view illustrating a clean water dispensing device according to the present invention.
Figure 3:
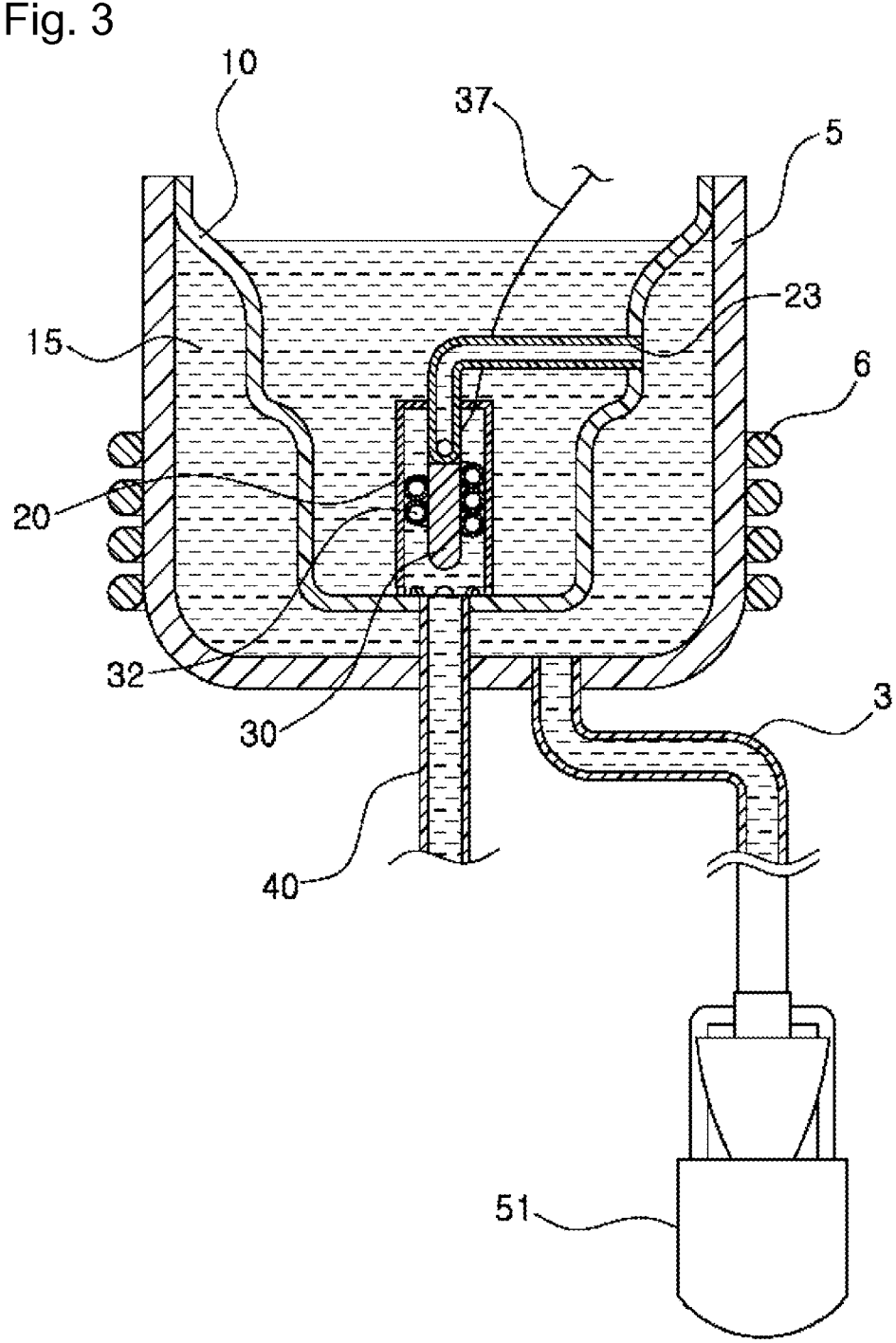
FIG. 3 is a sectional view illustrating the clean water dispensing device according to an embodiment of the present invention.
Figure 4:
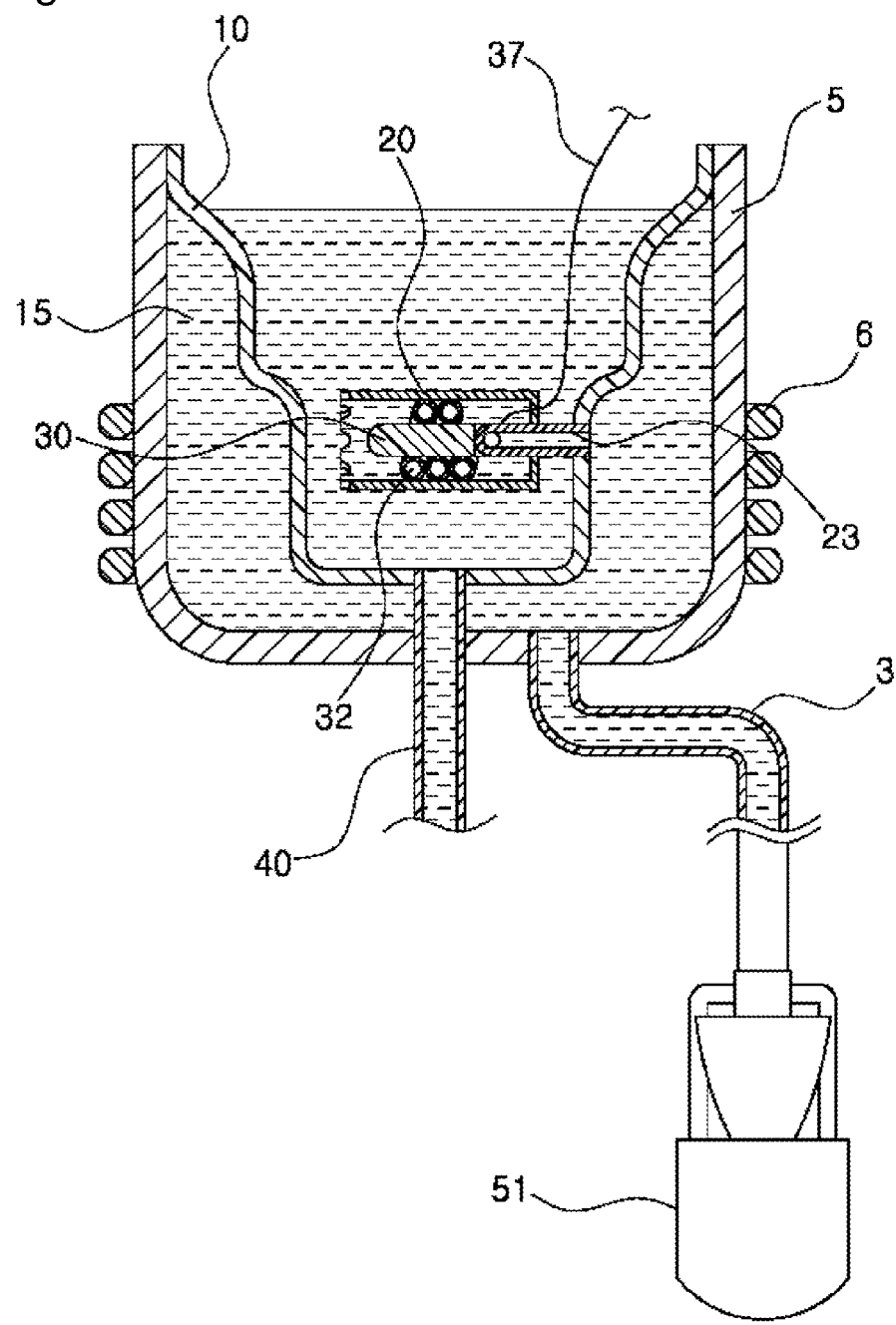
FIG. 4 is a sectional view illustrating a clean water dispensing device according to another embodiment of the present invention.
Figure 5:
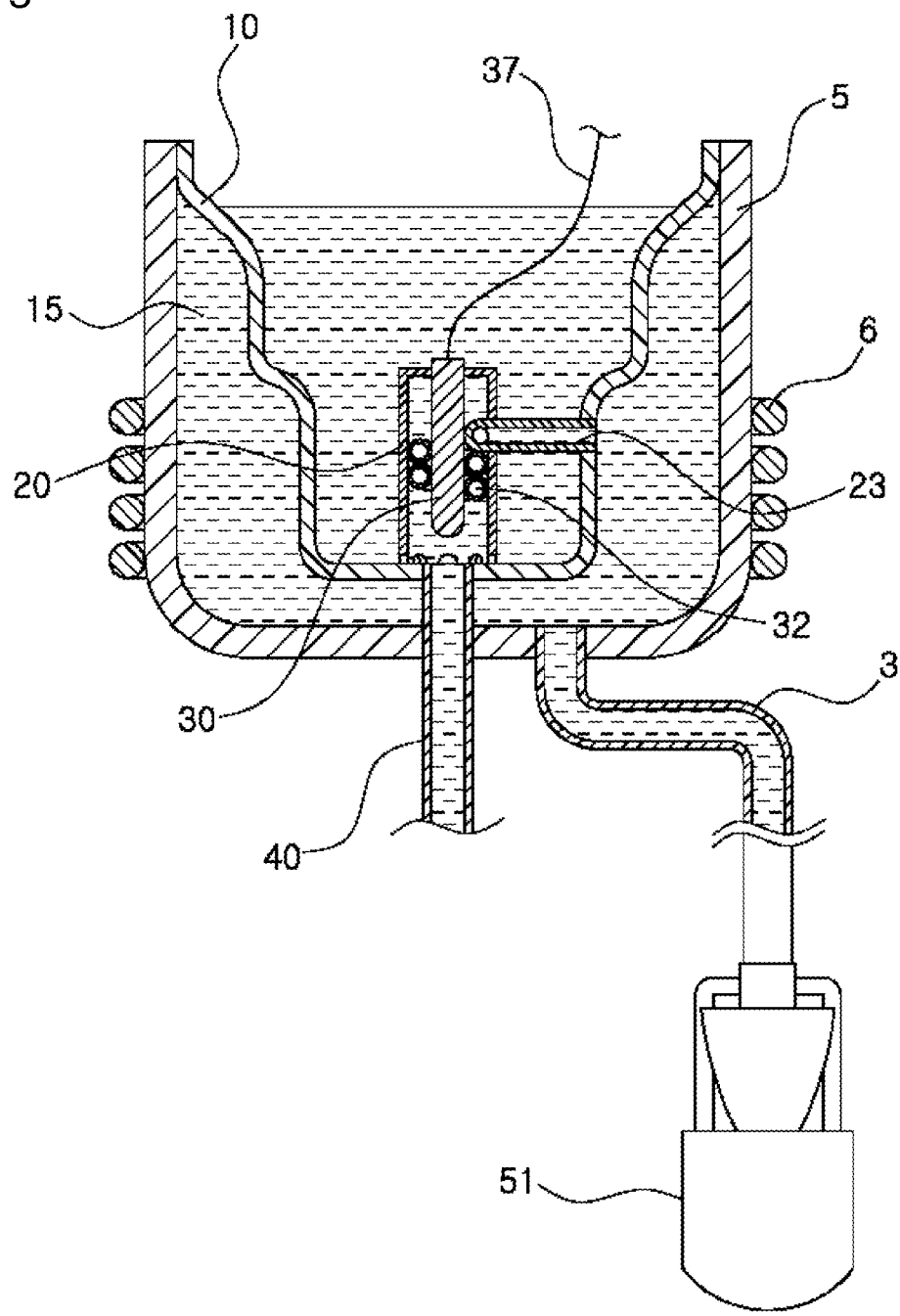
FIG. 5 is a sectional view illustrating a clean water dispensing device according to a further embodiment of the present invention.

Hereinafter, embodiments of the present invention will be described with reference to the attached drawings. If in the specification, detailed descriptions of well-known functions or configurations would unnecessarily obfuscate the gist of the present invention, the detailed descriptions will be omitted.

As shown in FIGS. 2 through 5, a clean water dispensing device for a cold and hot water dispenser or a water purifier according to an embodiment of the present invention includes: a pure water tank 10 which contains drinking water therein and is fitted into a cold water tank 5 in such a way that a closed space 15 is defined between the pure water tank 10 and the cold water tank 5 with cold water disposed in the closed space 15; a sterilization tube 20 which is provided in the pure water tank 10 and has an inlet port 21 that is open and an outlet port 23 connected to the closed space 15 through the pure water tank 10; a sterilization lamp 30 which is disposed in the sterilization tube 20; and a transit tube 32 which is spirally wound around an outer circumferential surface of the sterilization lamp 30 and is connected to the outlet port 23. The drinking water that is contained in the pure water tank 10 is drawn into the inlet port 21 and passes through the transit tube 32 before being supplied into the cold water tank 5 through the outlet port 23 and stored therein.

The pure water tank 10 that contains drinking water therein is fitted into the cold water tank 5, thus forming the space 15 between the pure water tank 10 and the cold water tank 5. Drinking water which enters the space 15 is cooled, and the cooled water (cold water) is stored in the space 15. An annular packing (not shown) is inserted into the junction between an inner surface of the cold water tank 5 and an outer surface of the pure water tank 10 so that the space 15 defined between the cold water tank 5 and the pure water tank 10 is isolated from outside air. Thanks to the structure of the space 15 being isolated from outside air, the cold water can be prevented from being contaminated by bacteria that is floating in the air.

The drinking water that is contained in the pure water tank 10, in the case of a cold and hot water dispenser, is mainly water supplied from a mineral water tank and, in the case of a water purifier, is water purified by a filter. Because the upper end of the pure water tank 10 is open, drinking water contained in the pure water tank 10 makes contact with the outside air, and bacteria may spread from the air to the drinking water and propagate in the drinking water. To prevent such propagation of bacteria, the sterilization lamp 30 is required in the pure water tank 10. Since the penetration distance of the sterilization lamp 30 is not comparatively deep, the sterilization tube 20 is also required in consideration of the penetration depth of the sterilization lamp 30.

The sterilization tube 20 that is disposed in the pure water tank 10 is open on a first end thereof to form the inlet port 21. The outlet port 23 formed on a second end of the sterilization tube 20 is connected to the space 15 through the pure water tank 10. Because of this structure, in order to store the drinking water that has been contained in the pure water tank 10 in the cold water tank 5, the drinking water must pass through the sterilization tube 20. In other words, the drinking water contained in the pure water tank 10 is drawn into the inlet port 21 before entering the cold water tank 5 through the outlet port 23.

Even if bacteria lives in the drinking water contained in the pure water tank 10, the bacteria is killed by the sterilization tube 20 while the drinking water passes through the sterilization tube 20. Therefore, sterilized clean water is stored in the space 15. Furthermore, because the space 15 is isolated from outside air, bacterial penetration does not occur. Therefore, although the drinking water is cooled in the cold water tank 5 and stored therein for a long period of time, there is no possibility of bacterial contamination.

The sterilization lamp 30 connected to a power wire 37 for power supply is disposed in the sterilization tube 20. Given the penetration depth of the sterilization lamp 30, the diameter of the sterilization tube 20 is determined. The transit tube 32 is provided between an inner circumferential surface of the sterilization tube 20 and the outer circumferential surface of the sterilization lamp 30, is spirally wound around the outer circumferential surface of the sterilization lamp 30, and is connected to the outlet port 23. Drinking water drawn into the inlet port 21 enters the cold water tank 5 through the outlet port 23 via the transit tube 32. Because the drinking water must pass through the transit tube 32 that is spirally wound around the outer circumferential surface of the sterilization lamp 30, the time period for which the drinking water is around the sterilization lamp 30 can be increased, whereby the sterilization effect can be markedly enhanced compared to that of the case where there is no transit tube.

Preferably, the transit tube 32 is made of a quartz tube. Furthermore, any material can be used so long as ultraviolet rays can pass through it. To facilitate connection between the transit tube 32 and the outlet port 23, a connection pipe (not shown) made of flexible material such as silicon may be used.

Although the sterilization lamp 30 is provided in the pure water tank 10, drinking water that is not near to the sterilization lamp 30 cannot be sterilized by the sterilization lamp 30. However, in the present invention, to transfer drinking water from the pure water tank 10 to the cold water tank 5, the drinking water must pass through the transit tube 32 which is disposed within the penetration distance range of the sterilization lamp 30. Therefore, drinking water that is stored in the cold water tank 30 can be effectively sterilized.

Furthermore, the sterilization tube 20 is placed upright in such a way that the inlet port 21 thereof is disposed at a lower position, and the outlet port 23 is disposed at an upper position. Thus, drinking water is drawn into the lower end of the sterilization tube 20 and is discharged out of the sterilization tube 20 through the upper end thereof while overcoming the force of gravity. Therefore, the time period for which drinking water is in the sterilization tube 20 is increased, thus further enhancing the sterilization effect.

Meanwhile, in the case where the inlet port 21 is brought into close contact with the bottom of the pure water tank 10, an inlet hole 22 is formed in the inlet port 21 so that drinking water can be drawn into the sterilization tube 20 through the inlet hole 22. Meanwhile, in this embodiment, a discharge pipe 40, which communicates with the pure water tank 10 and passes through the cold water tank 5, is coupled to a portion of the pure water tank 10. Drinking water is supplied into a hot water tank through the discharge pipe 40 and stored in the hot water tank. Therefore, compared to the typical cold and hot water dispenser in which cold water is supplied from the cold water tank 5 to the hot water tank, the cold and hot water dispenser having the clean water dispensing device according to the present invention can reduce consumption of power required to heat drinking water.

Mode for Invention

Figure 6:
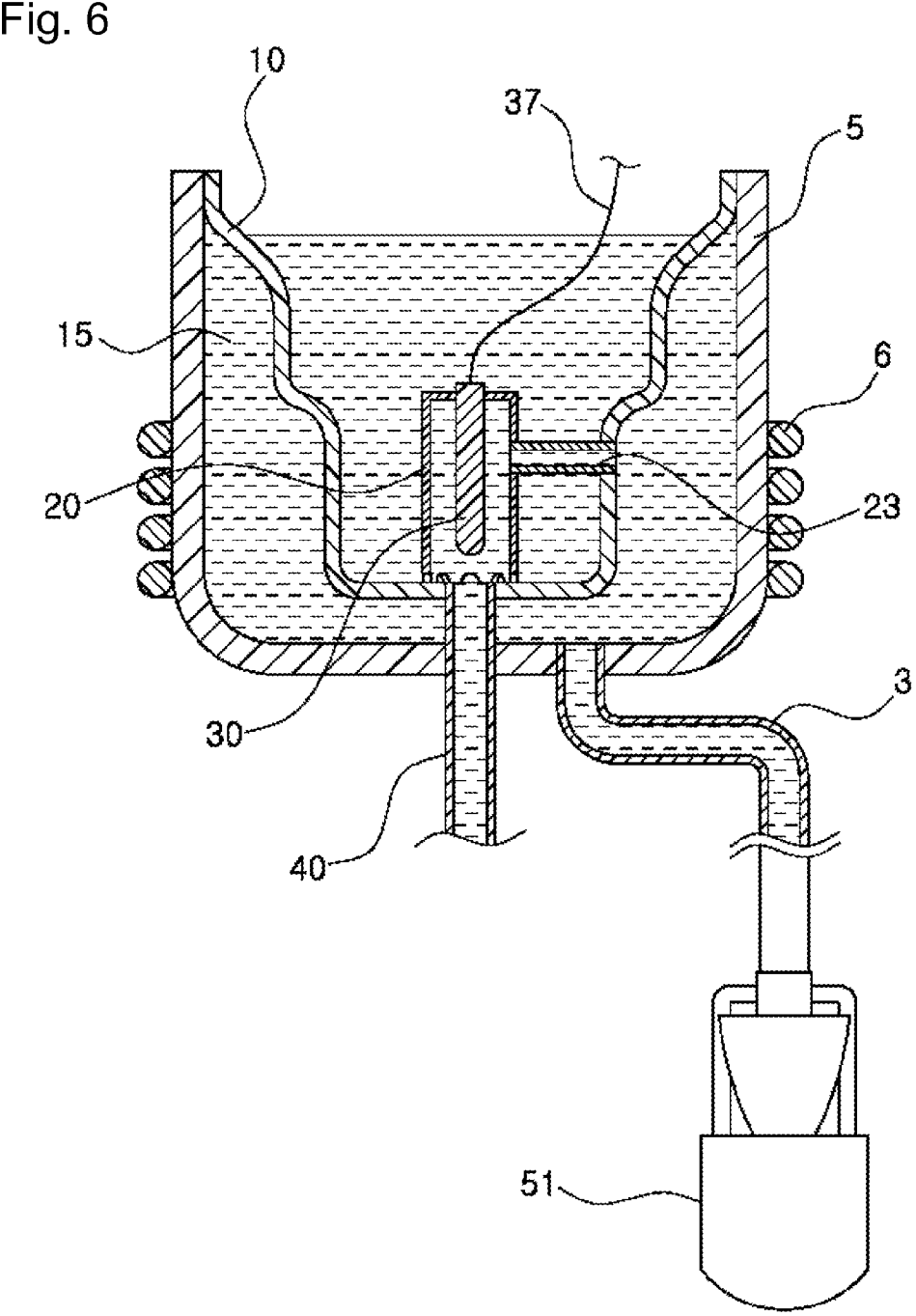
FIG. 6 is a sectional view of the clean water dispensing device from which a transit tube has been removed, according to the present invention.

FIG. 6 is a sectional view of the clean water dispensing device according to the present invention from which the transit tube has been removed. A clean water dispensing device for a cold and hot water dispenser or a water purifier according to an embodiment the present invention includes: a pure water tank 10 which contains drinking water therein and is disposed in a cold water tank 5 in such a way that a closed space 15 is defined between the pure water tank 10 and the cold water tank 5 with cold water disposed in the closed space 15; a sterilization tube 20 which is provided in the pure water tank 10 and has an inlet port 21 that is open and an outlet port 23 connected to the closed space 15 through the pure water tank 10; and a sterilization lamp 30 which is disposed in the sterilization tube 20. The drinking water that is contained in the pure water tank 10 is drawn into the inlet port 21 and is supplied into the cold water tank 5 through the outlet port 23 before being stored in the cold water tank 5.

INDUSTRIAL APPLICABILITY

As described above, in a clean water dispensing device according to the present invention, a pure water tank is fitted into the cold water tank in such a way that a closed space is defined between the cold water tank and the pure water tank and is isolated from outside air. Only drinking water that has been sterilized by a sterilization tube disposed in a pure water tank is supplied into the closed space, and is cooled and stored therein. Therefore, even if cold water is stored in the closed space for a long period of time, there is little possibility of the propagation of bacteria.

The invention claimed is:

1. A clean water dispensing device for a cold and hot water dispenser or a water purifier, the clean water dispensing device comprising:
   a pure water tank containing drinking water therein, the pure water tank being disposed in a cold water tank in such a way that a closed space is defined between the pure water tank and the cold water tank with cold water disposed in the closed space;
   a sterilization tube provided in the pure water tank, the sterilization tube having an inlet port that is open and an outlet port connected to the closed space through the pure water tank;
   a sterilization lamp disposed in the sterilization tube; and
   a transit tube spirally wound around an outer circumferential surface of the sterilization lamp, the transit tube being connected to the outlet port,
   wherein the drinking water that is contained in the pure water tank is drawn into the inlet port and passes through the transit tube before being supplied into the cold water tank through the outlet port and being stored in the cold water tank.

2. A clean water dispensing device for a cold and hot water dispenser or a water purifier, the clean water dispensing device comprising:
   a pure water tank containing drinking water therein, the pure water tank being disposed in a cold water tank in such a way that a closed space is defined between the pure water tank and the cold water tank with cold water disposed in the closed space;
   a sterilization tube provided in the pure water tank, the sterilization tube having an inlet port that is open and an outlet port connected to the closed space through the pure water tank; and
   a sterilization lamp disposed in the sterilization tube,
   wherein the drinking water that is contained in the pure water tank is drawn into the inlet port and is supplied into the cold water tank through the outlet port before being stored in the cold water tank.

3. The clean water dispensing device according to claim 1, wherein the sterilization tube is placed upright in such a way that the inlet port is disposed at a lower position, and the outlet port is disposed at an upper position, and
   the inlet port is brought into close contact with a bottom of the pure water tank, and an inlet hole is formed in the inlet port so that the drinking water is drawn into the sterilization tube through the inlet hole.

* * * * *